United States Patent [19]

Friedrich et al.

[11] 4,217,295

[45] Aug. 12, 1980

[54] PROCESS OF CATALYTIC METHANATION

[75] Inventors: Heinz G. Friedrich, Houston, Tex.; James V. Kennedy, Westfield, N.J.

[73] Assignee: NL Industries, Inc., New York, N.Y.

[21] Appl. No.: 816,534

[22] Filed: Jul. 18, 1977

Related U.S. Application Data

[63] Continuation of Ser. No. 596,518, Jul. 16, 1975, abandoned.

[51] Int. Cl.$^2$ ............................................. C01C 1/04
[52] U.S. Cl. ........................... 260/449.6 M; 252/455; 252/455 Z; 252/459; 252/458; 252/472
[58] Field of Search ................... 260/449 M, 449.6 M; 252/455 R

[56] References Cited

U.S. PATENT DOCUMENTS

| | | | |
|---|---|---|---|
| 3,379,505 | 11/1968 | Holmes et al. | 260/449 M |
| 3,625,665 | 12/1971 | Thompson | 260/449 M |
| 3,686,341 | 8/1972 | Eberly | 252/455 |
| 3,692,700 | 9/1972 | Sawyer et al. | 252/455 |
| 3,729,429 | 4/1973 | Robson | 252/455 |
| 3,730,694 | 5/1973 | Wunderlich | 260/449 M |
| 3,804,741 | 4/1974 | Robson | 252/454 |
| 3,838,041 | 9/1974 | Sawyer et al. | 252/455 |
| 3,844,978 | 10/1974 | Hickson | 252/455 |
| 3,844,979 | 10/1974 | Hickson | 252/455 |
| 3,901,667 | 8/1975 | Herrmann | 260/449 M |
| 3,947,483 | 3/1976 | Kobylinski et al. | 260/449 M |

FOREIGN PATENT DOCUMENTS

| | | | |
|---|---|---|---|
| 1645840 | 7/1970 | Fed. Rep. of Germany | 260/449 M |
| 1523687 | 5/1968 | France | 260/449 M |

OTHER PUBLICATIONS

Mill's et al., Catalyst Reviews, 8 (2) 181, 1973.

*Primary Examiner*—Howard T. Mars
*Attorney, Agent, or Firm*—Gary M. Nath; Malcolm L. Sutherland; Roy F. House

[57] ABSTRACT

Methanation of carbon oxides such as carbon monoxide and carbon dioxide with hydrogen to produce methane is carried out with the aid of a heated catalyst which is the calcination product of a serpentine containing nickel and optionally magnesium and other elements together with silicon in the essentially laminar nickel serpentine. The catalysts exhibit good conversion at relatively low temperatures, are relatively insensitive to high temperature excursions, and have an extended life.

17 Claims, No Drawings

PROCESS OF CATALYTIC METHANATION

This is a continuation of application Ser. No. 596,518, filed July 16, 1975 now abandoned.

This invention relates to the methanation of oxides of carbon to produce methane by a procedure utilizing a novel catalyst for this reaction. More particularly, it relates to the utilization of certain heavy metal substituted serpentines as precursors of finished catalysts whereby the reaction between oxides of carbon such as carbon monoxide and carbon dioxide with hydrogen to produce methane may be carried out under especially favourable process conditions, including but not limited to high conversion rates, low conversion temperatures, long catalyst life, and relatively insensitivity of the catalyst to high temperature excursions.

The production of methane from oxides of carbon by a catalytic route has been known since 1902, and has been employed to a certain extent in the intervening years. However, with the current shortage of all forms of energy, the reaction has achieved great importance, inasmuch as it promises a solution to the shortage of natural gas by enabling coal, lignite, and petroleum fractions and residues not otherwise readily utilizable to serve as the ultimate source of the carbon oxides which are reacted with hydrogen to form methane (and water as the principal secondary product). The reaction concerned is commonly called methanation, and a vast literature exists on the subject extending back nearly to the commencement of the present century. Useful articles are Chapters 1 and 6 on pages 1–27 and 473–511 respectively of Volume IV of the series entitled "Catalysis", edited by Paul H. Emmett, New York, Reinhold, 1956. More recent reviews, showing in addition the overall process commencing with coal or naphtha, may be found in the journal *Hydrocarbon Processing*, Apr., 1973, pages 117 through 125; and *The Oil and Gas Journal*, June 25, 1973, pages 107–134. Another useful paper is *Catalysis Reviews* 8 [2]159–210 (1973). All of these articles are hereby incorporated herein by reference.

The present invention deals with the final catalyzed reaction in such composite processes to obtain methane from low grade raw materials. It also finds utility wherever carbon oxides are to be converted to methane, as for example in the purification of synthesis gas where the impurities consist of carbon monoxide or carbon dioxide or mixtures of the two.

Generally speaking and in accordance with illustrative embodiments of our invention, in the process of methanation wherein a carbon oxide or mixture of carbon oxides are catalytically hydrogenated so as to form methane by passing the carbon oxides together with hydrogen over a heated catalyst, our invention provides the improvement which comprises utilizing as the catalyst a heavy metal silicate resulting from the calcination and reduction of a nickel serpentine having a chemical composition represented by the following:

$$(Ni_yR_gM_{6-y-g})\cdot(R_hSi_{4-h})O_{10}(OH,F)_8$$

wherein:

M is Mg, Co++, Fe++, Cu++, Mn++, Zn++, or mixtures thereof;

R is Al, Cr++, or mixtures thereof;

$$g+h=2x,$$

$$0 \leq x < 0.1;\ 0.5 \leq y \leq 6;$$

and wherein the first parenthesis shows the cations in the octahedral layer and the second parenthesis shows the cations in the tetrahedral layer; and wherein from zero to two fluoride ions may be present for a total of eight hydroxide plus fluoride; [1] this precursor nickel serpentine prior to calcining being a 1:1 trioctahedral phyllosilicate in general having a substantially balanced framework, from the standpoint of total charge, with no exchangeable ions needed for neutrality. In this formulation, any ions exterior to the lattice which may be required to neutralize any slight electrostatic imbalance in the lattice proper have not been indicated, since they are non-essential.

In general, and in the "ideal" serpentine, $g \approx h \approx x$, so that the first line of the formula reduces to:

Since x is at most about one-fortieth of the silicon present (on an atomic basis) and at most about one-sixtieth of the combined nickel and M atoms, it will be clear that the distribution of x as between g and h requires highly exacting structural determinations. On the other hand, the gross content of Si, Ni, M and R, as well as of the remaining elements, can be readily determined by standard chemical methods; and likewise the a, b, and c lattice parameters discussed below can be readily determined by standard x-ray diffraction methods, so that the correspondence or non-correspondence of a given preparation or mineral specimen to Formula [1] can easily be determined without separately determining g and h, particularly since their sum, 2x, readily follow from the standard chemical and x-ray investigations just mentioned.

An alternative formulation, which upon mere inspection will be seen to be completely equivalent to the foregoing [1], is that the chemical composition corresponds to one of the two end members shown below or to any composition intermediate therebetween, viz:

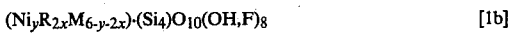

and

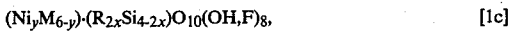

all of the other restraints shown for [1] of course applying.

A typical and indeed expected intermediate composition between end members, [1b] and [1c] appears hereinabove as [1a].

As is known, nickel serpentines are phyllosilicates, that is, silicates with a laminar habit, exhibiting a basal spacing, i.e., a c spacing, approximately 7 Å. The a spacing is about 5.3 Å, or a multiple thereof, while the b spacing is about 9.2 or 9.3 Å. Moreover, they are silicates of the so-called 1:1 type, having one octahedral layer bonded to an adjacent tetrahedral layer by the sharing of oxygen ions. Moreover, the structure is trioctahedral; that is, all of the possible sites for positive ions in the octahedral layer are occupied, in contrast to the so-called dioctahedral structures of some other phyllosilicates in which only ⅔ of such sites are filled. Furthermore, each individual 1:1 sheet is electrostatically substantially neutral, with as many positive ions as negative ions within the combined 1:1 layer structure. This is in contrast to electrostatically unbalanced silicates, such as zeolites and smectites, which require cations exterior to the silicate framework in order to achieve electrostatic neutrality. Those knowledgeable in clay chemistry will of course recognize that some ion-exchange capacity is generated by broken bonds at the edges of the crystallites even in balanced layers, as evidenced for example by kalolinite and attapulgite.

A good discussion of serpentines (including nickel serpentines) occurs in the chapter by that name on pages 170-190 of the text "Rock-Forming Minerals", volume 3, Sheet Silicates, by W. A. Deer et al., London, 1962. Nomenclature for this group varies somewhat; Brindley in the text, "The X-Ray Identification and Crystal Structures of Clay Minerals", G. Brown, Ed., London, 1961, pages 109-131, adopts the term "nickel serpentine". French workers prefer "nickeliferous antigorite", as described, for example, on pages 180-193 of the text "Minéralogie des Argiles", by Simonne Caillère et al., Paris, 1963. The cited chapters in these three texts are hereby incorporated herein by reference.

Nickel serpentines within the scope of the invention occur in a number of localities throughout the world, some in quality and quantity of such a nature to be commercial. The nickel ores of New Caledonia are largely nickel serpentines, and individual species thereof have been called nepouite, noumeite, and others. Another well-known deposit occurs near Riddle, Oregon, and has been generally identified as garnierite. Typical analyses of the New Caledonian and Oregonian nickel serpentines are given in U.S. Geological Survey Bulletin No. 770, 1924, p. 712. It will be readily understood that all minerals which may be termed nickel serpentines may not necessarily have a composition coming within the scope of formula [1] set forth herein above; an analysis an inspection will of course settle the point in any given case.

In addition to naturally occuring nickel serpentines, a vast literature, both scientific and patent, exists disclosing various methods for synthesizing nickel serpentines, and moreover, for synthesizing nickel serpentines within the scope of the invention provided that the starting materials and processing conditions are such that a synthesized product coming within the scope of formula [1] results.

Some of the relevant literature of this type comprises the following articles:

*C.R. Acad. Sci., Paris,* Serie C 264 [18] 1536-8 (1967)
Martin, G. A., et al. Sur la preparation et la structure de l'antigorite et de la montmorillonite de nickel.
*Ibid.,* 225, 869-72 (1947)
Longuet, J., et al.
Synthese de silicates de nickel, magnesium et cobalt, presentant des structures du type kaolinite-antigorite.
*Ibid.,* 239, 1535-1537 (1954)
Caillere, S., et al.
Synthese des quelques phyllites nickeliferes.
*Ibid.,* 241, 810-812 (1955)
Caillere, S., et al.
Influence de la temperature . . . formation de l'antigorite nickelifere.
*Ibid.,* Serie C 267, 610-613 (1968)
Dalmon, A., et al.
Sur la préparation et la structure des silicates basiques de
cobalt et de magnésium du type talc et antigorite.
*Journal de Chemie Physique et de Physicochimie Biologique* 67 (b) 1149-60 (1970)
Martin, G. A., et al.
Synthèse du talc et de l'antigorite de nickel, étude de leur décomposition thermique et de leur réduction en vue
d'obtenir des catalyseurs de nickel sur silice.
*Helv. Chim. Acta* 25 1543-47 (1942)
Feitknecht, W., et al.
Über die Bildung eines Nickel- und Kobaltsilicates mit Schichtengitter
*Naturwissenschaften* 39, 233-34, (1952)
Noll, W., et al.
Synthese des Garnierites
*American Mineralogist* 39: 957-75, (1954)
Roy, Della M., et al.
An Experimental Study of the Formation and Properties
of Synthetic Serpentines and Related Layer Silicate Minerals.
*Clay Minerals Bulletin,* 5, [no.30] 272-278 (1963)
Caillere, S., et al.
Nouvelles Etudes sur la Synthese des Minerzux Argileux a partir de gels.
*Trans. 4th Intern. Congr. Soil Sci.,* Amsterdam 3, 34-37;
Franzen, P., et al.
Synthesis of Nickel Hydrosilicates
*Bull. Grp. Franc. Argiles* 7, [2] 21-30 (1956)
Caillère, S., et al.
Étude de Quelques Silicates Nickélifères Naturels et de Synthese
*Contr. Mineral and Petrol.* 34 84-86 (1972)
Jasmund K., et al.
Synthesis of Mg- and Ni-Antigorite
*Ibid.,* 34 346 (1972)
Jasmund, K., et al.
Synthesis of Mg- and Ni-Antigorite: A Correction
*Beitrage zur Mineralogie und Petrograpie* 7, 232-241 (1960)
Noll, W., et al.
Ueber synthetischen Kobaltchrysotil und seine Beziehungen usw.
*Bul. Soc. Franc. Miner. Crist.* 79, 408-420 (1956)
Caillère, S., et al.
Étude Expérimentale du mécanisme de la formation des antigorites
nickélifères.
*Kolloïd-Zeitschrift* 157, 1-11 (1958)
Noll, W., et al.
Adsorptionsvermoegen und spezifische Oberflaeche von Silikaten mit
roehrenforemig gebauten Primaerkristallen.
*Rec. trav. chim.* 70, 793-812 (1951)
van Voorthuijsen et al.
Structure and properties of compounds formed during the preparation
of nickel-on-silica catalysts.

Typical of the patent literature containing procedures for synthesizing nickel serpentines and other so-called nickel serpentine minerals are the following:

| U.S. Pat. No. | | |
|---|---|---|
| 2,658,875 | Schuit, et al., | November 10, 1953 |
| 3,686,341 | Eberly | August 22, 1972 |
| 3,686,348 | Eberly | August 22, 1972 |
| 3,692,700 | Sawyer et al. | September 19, 1972 |
| 3,729,429 | Robson | April 24, 1973 |
| 3,804,741 | Robson | April 16, 1974 |

| 3,838,041 | Sawyer et al. | September 24, 1974 |

The precursor nickel serpentines are made by a hydrothermal process; or they may be naturally occuring nickel serpentines corresponding to the foregoing description, to the extent that commercially workable deposits thereof are available to those desiring to practice the invention, as already discussed. In general we prefer to synthesize nickel serpentines inasmuch as better control may then be had over the properties of the final product, with particular reference to such features as chemical composition, particle configuration, surface area, and the like.

When the precursor nickel serpentines are to be obtained by synthesis, a procedure selected from the extensive prior art syntheses listed hereinabove may be used. A general procedure which we prefer may be carried out as follow:

In general, relatively simple sources of the various elements present in the desired product and an alkali such as sodium hydroxide are added to water. The well-homogenized mixture is placed in a sealed pressure vessel, which is then brought to a preselected temperature, typically 250° C. to 350° C., and maintained there for a preselected period of time, typically one-half or 6 or even 72 hours, after which the vessel is cooled and the contents removed, and, if desired or necessary, washed free of soluble salts and dried. Agitation during the hydrothermal processing is generally desired in large-scale preparations. The product is conveniently examined by x-ray diffraction as a check on any given run.

A general feed formula utilizing soluble salts is as follows: $yNiCl_2 \cdot (6-y-x)MgCl_2 \cdot 2xAlCl_3 \cdot (4-x)SiO_2 \cdot (12+4x+\beta) \cdot NaOH \cdot nH_2O$ where $\beta$ is the mols of base in excess of that necessary to precipitate all multivalent metals as their oxides or hydroxides, and where n is approximately 200–350, preferably about 250.

The values of x and y are the same as those set forth in the nickel serpentine formula [1] given earlier in this disclosure; we have found that the synthesized products exhibit substantially the same ratio of metal constituents as is present in the feed mixture, so that the values of x and y are the same for both feed and product; and are subject to the same restraints as already given in formula [1]. For the NaOH there may be substituted KOH, LiOH, NH$_4$OH, ½ Ca(OH)$_2$, or mixtures thereof, or like alkalizing agent.

The foregoing feed formula shows the various metals added as their chloride salts. This is in general preferred, although other salts may be used, such as the citrate, acetate, nitrate, and the like.

In general, $\beta$ in formula [2] above may vary from zero to as high as about 20, the higher values of $\beta$ being practical for weak bases such as NH$_4$OH. For strong bases a $\beta$ value higher than 6 is scarcely needed.

The constituents, save for the caustic and a minor portion of the added water, are conveniently placed in a suitable mixing device and homogenized, after which the caustic is added in solution with continued mixing. For small-scale laboratory runs, a silver-lined stainless steel pressure vessel with a capacity of about 15 ml may be used, and heated in an oven. For batches of larger size, autoclaves of suitable capacity may be used.

The feed formula just given does not recite fluoride, which, of course, is present whenever this optional component is desired to be present. When this is the case, we find it best to add fluoride as sodium fluoride to the feed mixture without attempting to reduce the amount of caustic to compensate. Indeed, quite in contrast to the metallic ions, not all of the fluoride ions present in the feed mixture ultimately become part of nickel serpentine lattice, so that it is necessary to use a considerable excess of sodium fluoride. Up to six or eight mols of sodium fluoride per formula weight in the feed may for example be used which will still result in somewhat less than one mol of fluoride becoming part of the lattice; that is, slightly less than one hydroxyl will be isomorphously substituted by fluoride. More sodium fluoride may of course be used, leading to a higher degree of substitution.

Consideration of the formulas for the feed and for the synthesized product will make it evident that soluble salts, for the most part sodium chloride, will appear as an admixture with the product when this type of feed mixture is used. In general it is desirable to separate out the soluble salts by thorough washing with water. The washed product may then be dried, and if desired, ground.

The silica may be added in any convenient form, such as polysilicic acid, which may be made in accordance with U.S. Pat. No. 3,649,556 to Hoffman. Alternatively, sodium silicate solution may be used, taking into account the caustic soda equivalent thereof. The alumina is conveniently any finely-divided reactive form thereof, such as luminum hydroxide, sometimes termed alumina trihydrate.

When the synthetic procedures set forth in the prior art articles and patents cited hereinabove are employed, due consideration should of course be given to the compositional restraints specified in accordance with the invention.

The nickel serpentines may also be readily synthesized by using a feed mixture in which the various components are added in the form of their oxides, basic oxides, or carbonates, without added alkali as such. This obviates the necessity for washing the product free of soluble salts. Examples showing this synthetic route will be given hereinbelow.

As we have explained hereinabove, in order to form our inventive catalysts we calcine and reduce the selected nickel serpentines so that their crystallinity is destroyed, which may be termed "amorphous". One must, of course, understand that this by no means implies that the structure is utterly random. To the contrary, the relative dispositions of the component ions have been conditioned by their previous crystalline structure while in the precursor serpentine state. However, in view of the number of different atomic species present, it is quite beyond present-day technology to determine precisely what those dispositions are, so that the inventive catalysts can only be characterized in terms of their crystalline precursors and of the processing by way of calcination and reduction.

It will be understood that by "amorphous" we refer to the essential non-appearance of the characteristic serpentine structure in the x-ray diffraction pattern, although diffuse metal oxide crystal patterns may appear, as for example bunsenite, i.e., nickel oxide, after calcination, and crystalites of metallic nickel after reduction.

The temperature required for calcination can of course be readily determined by pilot tests; a temperature of about 700° C. to about 750° 1 C. will be found adequate, although the effective range varies from about 500° C. to about 900° 1 C. The calcined product is then reduced by heating in a reducing, preferably hydrogen, atmosphere at an effective reducing temperature, which is found to be from about 500° C. to about 900° C. In both steps, the duration should be long enough to obtain the desired degree of reduction. Generally, three hours at 705° C. is adequate for calcination, and five or more hours at 650° C. for reduction, the hydrogen, preferably at a minimum of one atmosphere. It will be appreciated that these temperatures and times are given by way of example and not by way of limitation. Simple preliminary tests well known to those in the x-ray diffraction and catalytic arts will provide satisfactory processing conditions for any given case. The calcination and reduction can be conducted concurrently by heating the serpentine at a temperature above about 500° C. in the presence of hydrogen. In general, however, the serpentine is less easily reduced than the amorphous calcined serpentine and longer reduction times are necessary when the serpentine is not calcined before reduction.

We now give some examples showing the practice of our invention:

EXAMPLE 1

Four mols of polysilicic acid, made as described in U.S. Pat. No. 3,649,556, and six mols of nickel carbonate (materials assaying 80.77% $NiCO_3$ was used) were made into a slurry with water at 15% total solids by weight with a highspeed mixer. The slurry was placed in an autoclave and maintained at 300° C. for four hours. The apparatus was then cooled, and the nickel serpentine recovered. It had the following formula:

$(Ni_6) \cdot (Si_4) O_{10}(OH)_8$.

Separate portions of the product were reslurried with various clay binders in the proportion of 80% by weight of the nickel serpentine and 20% of the selected clay, using water and a laboratory mixer, and then dried, calcined at 705° C. for three hours, and ground to 30/60 mesh. One portion was also used without admixture, as the pure nickel serpentine. The samples thus prepared were given the following designations:

| Sample | Clay Binder |
|---|---|
| 1 A | None |
| 1 B | kaolinite, from Georgia, U.S.A. |
| 1 C | saponite, made as described in U.S. 3,855,147 (a = O, x = 1.43, y = O) 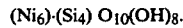 |
| 1 D | sepiolite, from Nevada, U.S.A. |
| 1 E | hectorite, from California, U.S.A. |
| 1 F | attapulgite, from Georgia, U.S.A. |
| 1 G | montmorillonite, from Wyoming, U.S.A. |

The samples prepared as described above were then tested for their activity as methanation catalysts. 8.4 cc of each sample were placed in the reactor tube and reduced by heating in a hydrogen atmosphere for sixteen hours at 650° C., the hydrogen being passed through the sample (having a mesh size of passing 30 and retained on 60 U.S. Standard mesh) at a rate of 40 cc per minute. Subsequently, commencing at a temperature of aout 200° C., a mixture of approximately 20 mol % carbon monoxide and 80 mol % hydrogen was passed through the catalyst charge in the reactor, the latter being provided with sufficient instrumentation to determine temperatures, flow rates, and input and output gas compositions, and thus the percent conversion of the carbon oxide to methane. The temperature was raised in steps at approximately thirty-minute intervals, to a maximum in general of about 600° C. The input gas hourly space velocity (the volume of gas per volume of catalyst charge, per hour, at standard temperature and pressure) was 1500.

After the sequence of methanation tests just described had been completed for a given sample, the catalyst charge was again reduced in hydrogen overnight at 650° C. and then for three hours at 850° C. After cooling to 200° C., a second series of methanation tests were commenced and carried out as before, ending usually at about 600° C.

Results of the tests are given below in Table I, while some typical gas composition data for some of the runs are given in Table II.

Table 1

| Sample | Gm Ni in 8.4 cc Charge | Minimum temperature, degree C.,: | |
|---|---|---|---|
| | | For 100% CO conversion, Catalyst reduced at 650° C. | For ≧ 90% CO conv. Catalyst reduced at 850° C. |
| 1 A | 3.16 | 235 | 470 |
| 1 B | 2.61 | 220 | 250 |
| 1 C | 2.32 | 202 | 315 |
| 1 D | 1.90 | 202 | 310 |
| 1 E | 2.74 | 243 | 405 |
| 1 F | 2.11 | 240 | 320 |
| 1 G | 2.38 | 220 | 300 |

Table II

| Sample No. | | °C. of run | Exit gas composition, mol percent | | | | Percent CO conversion |
|---|---|---|---|---|---|---|---|
| | | | CO | $H_2$ | $CH_4$ | $CO_2$ | |
| 1 A | * | 235 | 0.02 | 50.5 | 49.1 | 0.34 | 99.97 |
| | * | 393 | 0 | 50.7 | 49.3 | 0 | 100 |
| | * | 590 | 0.15 | 60.4 | 38.5 | 1.0 | 99.6 |
| | ** | 470 | 1.5 | 64.5 | 26.4 | 7.6 | 95.8 |
| | ** | 600 | 0.3 | 61.4 | 36.5 | 1.9 | 99.3 |
| 1 B | * | 220 | 0.06 | 55.21 | 42.23 | 2.49 | 99.9 |
| | * | 235 | 0 | 55.1 | 44.7 | 0.21 | 100 |
| | * | 500 | 0 | 57.7 | 42.3 | 0.02 | 100 |
| | * | 600 | 0.31 | 53.9 | 44.1 | 1.7 | 99.3 |
| | ** | 250 | 0 | 64.3 | 30.5 | 5.2 | 100 |
| | ** | 600 | 0 | 58.8 | 41.1 | 0.1 | 100 |
| 1 C | * | 202 | 0 | 60.8 | 37.8 | 1.5 | 100 |
| | * | 398 | 0 | 59.6 | 40.4 | 0 | 100 |
| | * | 595 | 0 | 67.2 | 32.8 | 0.05 | 100 |
| | ** | 315 | 0 | 57.4 | 39.6 | 3.0 | 100 |
| | ** | 585 | 0 | 59.3 | 40.2 | 0.52 | 100 |
| 1 D | * | 202 | 0 | 49.6 | 49.2 | 1.2 | 100 |
| | * | 495 | 0 | 46.4 | 53.6 | 0.03 | 100 |
| | * | 569 | 0.27 | 54.6 | 43.5 | 1.7 | 99.4 |
| | ** | 310 | 0 | 60.8 | 33.1 | 6.1 | 100 |
| | ** | 580 | 0 | 53.8 | 44.7 | 1.6 | 100 |
| 1 E | * | 243 | 0.14 | 51.6 | 47.0 | 1.2 | 99.7 |
| | * | 410 | 0 | 51.3 | 48.7 | 0 | 100 |
| | * | 610 | 0 | 56.6 | 42.9 | 0.6 | 100 |
| | ** | 405 | 0 | 50.5 | 48.3 | 1.2 | 100 |
| | ** | 500 | 0 | 48.3 | 51.7 | 0 | 100 |
| | ** | 600 | 0 | 59.1 | 40.7 | 0.2 | 100 |
| 1 F | * | 230 | 0.9 | 52.8 | 43.3 | 3.0 | 98.2 |
| | * | 245 | 0 | 49.2 | 47.8 | 3.0 | 100 |
| | * | 600 | 0 | 49.3 | 49.1 | 1.6 | 100 |
| | ** | 320 | 0 | 59.8 | 34.3 | 5.9 | 100 |
| | ** | 520 | 0 | 47.6 | 52.2 | 0.2 | 100 |
| | ** | 610 | 0 | 52.5 | 46.6 | 1.0 | 100 |

* Runs on catalyst reduced at 650° C.
** Runs on catalyst reduced at 650° C. overnight and at 850° C. for three hours.

One may see from Tables I and II that this nickel serpentine is an excellent methanation catalyst, giving substantially complete conversion of carbon monoxide at a low temperature, viz., 235° C. Moreover, even after being subjected to the high temperature of 850° C. it is still a good catalyst giving nearly complete conversion at 470° C. Still further, it operates well over the range up to about 600° C., whether it was reduced at 650° C. or 850° C. The criterion is whether the reaction between the hydrogen and the carbon monoxide has been catalyzed to give essentially equilibrium conversion of the starting materials, which is herein termed complete, or 100%, conversion. The thermodynamics of the reaction are more favorable at lower temperatures. In addition, low operating temperatures have obvious advantages in equipment simplification and longer expected life. However, the reaction should not be conducted below about 200° C. because of the formation of nickel carbonyl at lower temperatures.

Table II illustrates an important aspect of the invention, in accordance with which the nickel serpentine is intimately admixed with up to about its weight of a water dispersible clay mineral, preferably by wet mixing and subsequent drying. Suitable such clay minerals include montmorillonite, biedellite, kaolinite, halloysite, saponite, sepiolite, hectorite, attapulgite, illite, and others. To be sure, the clay, particularly when incorporated in the fashion described, imparts strength and mechanical integrity to the catalyst particles, but it is surprising and entirely unexpected that the clay addition causes the catalyst to give complete conversion at lower temperatures than otherwise, even when the clay-bearing nickel serpentine catalyst is reduced at the high temperature of 850° C. The latter is of practical importance because momentary high excursions of temperature are well-nigh unavoidable in plant operation, and a good catalyst should remain undamaged when so treated Thus, considering Tables I and II, it may be seen that 20% by weight of kaolinite lowers the 100% conversion temperature from 235° C. to 220° C., and even more importantly lowers the complete conversion temperature after the 850° C. treatment from 470° C. to 250° C. Similar beneficial effects may be observed for the other four clays used as binders in the runs of 1 B through 1 F.

Of course, more than one clay mineral may be used in a single preparation. For example, the nickel serpentine prior to calcination may be intimately admixed with up to its own weight of a mixture of equal parts of kaolinite and montmorillonite; or a mixture of equal parts of saponite and attapulgite, or in other proportions, and so forth, all preferably by wet mixing.

The tables are also exemplary of the circumstance that the methanation resulting from the hydrogenation should be carried out at at least 200° C. (to avoid nickel carbonyl formation) but in any case at a temperature high enough to effect substantial methanation of the carbon oxide or carbon oxides involved. The latter temperature varies from one calcined and reduced nickel serpentine to another, as is evident from the test resuts given hereinabove, and elsewhere herein.

EXAMPLE 2

The tests just as described were carried out on a further series of mixtures of the same nickel serpentine (designated as 2-A) with different proportions of montmorillonite, in the form of Wyoming bentonite fully converted to the sodium form and freed of dross by supercentrifuging, ion exchanging, and spray drying. These catalysts were calcined at 705° C. for three hours, ground to 30/60 mesh, and reduced overnight, as before, at 650° C. After methanation testing, the catalysts were reduced at 650° C. overnight and at 900° C. for three hours before additional methanation testing was undertaken. The results follow:

Table III

| Sample | % by weight Montmorillonite | Methanation Activity: Minimum °C. for ≧ 90% CO Conversion * | ** |
|---|---|---|---|
| 2 A | 0 | 225 | *** |
| 2 B | 5 | 210 | 250 |
| 2 C | 10 | 220 | 300 |
| 2 D | 20 | 215 | 250 |
| 2 E | 25 | 215 | 215 |
| 2 F | 30 | 235 | 250 |
| 2 G | 50 | 235 | *** |

\* Catalyst reduced at 650° C. overnight
\*\* Catalyst reduced at 650° C. overnight and then for three hours at 900° C.
\*\*\* Maximum conversion < 90% occured at 600° C.

Table III shows that montmorillonite shares the properties of the other clays listed for samples 1B through 1F of reducing the effective methanation temperature, both when reduced at 650° C. and at 900° C. It will be recalled that samples 1B through 1F contained 20% clay and 80% nickel serpentine. The results shown in Table III for samples 2B through 2G exhibit the effect of varying clay content over a wide range. At 50% montmorillonite (sample 2G) the activity of the catalyst reduced at 900° C. is poor, but the 235° C. figure for the catalyst reduced at 650° C. is remarkable, considering that this sample has only half as much of the nickel serpentine (before calcining) as sample 2A. It would appear that some synergistic action occurs between the clay and the nickel serpentine to account for this extraordinary behavior, since clay minerals by themselves have substantially no methanation activity.

EXAMPLE 3

The synthesis described in Example 1 was carried out using, in addition to the polysilicic acid and nickel carbonate, magnesium oxide and alumina. The molar ratios of the several components were in the same proportion as the nickel serpentine formed, viz.:

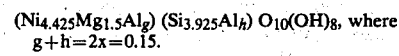

$(Ni_{4.425}Mg_{1.5}Al_g)(Si_{3.925}Al_h)O_{10}(OH)_8$, where $g+h=2x=0.15$.

Methanation tests and catalyst preparation as described in Example 2 were carried out on the sample, with the following results.

Table IV

| °C. of run | | Exit gas composition, mol percent | | | | Percent CO Conversion |
|---|---|---|---|---|---|---|
| | | CO | H$_2$ | CH$_4$ | CO$_2$ | |
| 220 | * | 0.1 | 57.9 | 39.0 | 3.0 | 99.7 |
| 300 | * | 0.0 | 50.8 | 48.8 | 0.4 | 100. |
| 400 | * | 0.0 | 48.9 | 50.9 | 0.2 | 100. |
| 500 | * | 0.0 | 50.6 | 48.7 | 0.8 | 100. |
| 600 | * | 1.0 | 56.6 | 39.1 | 3.3 | 97.6 |
| 300 | ** | 0.2 | 56.6 | 39.9 | 3.4 | 99.7 |
| 400 | ** | 0.0 | 55.0 | 42.3 | 2.6 | 100 |
| 500 | ** | 0.1 | 53.3 | 44.9 | 1.7 | 99.9 |
| 600 | ** | 1.2 | 57.3 | 37.8 | 3.7 | 97.3 |

\* Runs on catalyst reduced at 650° C.
\*\* Runs on catalyst reduced at 650° C. overnight and then at 900° C. for three hours.

It will be seen that this nickel serpentine was likewise the precursor of an excellent methanation catalyst.

EXAMPLE 4

A series of nickel serpentines were prepared by hydrothermal synthesis for four hours at 300° C., with varying amounts of nickel per unit cell. The general procedure was that of Example 1. Table V which follows, gives the grams of the starting materials, all batches being made up to 15% total solids. Also shown are the expected unit cell compositions of the products.

Table V

| Sample No. | $SiO_2$ (1) grams | $NiCO_3$ (2) grams | MgO (3) grams | Unit Cell Composition |
|---|---|---|---|---|
| 3A | 1200 | 4060 | 100 | $(Ni_{5.5}Mg_{0.5})Si_4O_{10}(OH)_8$ |
| 3B | 82.4 | 236.9 | 14.4 | $(Ni_5Mg)Si_4O_{10}(OH)_8$ |
| 3C | 135.6 | 373.2 | 35.2 | $(Ni_{4.5}Mg_{1.5})Si_4O_{10}(OH)_8$ |
| 3D | 145.8 | 268.3 | 76.7 | $(Ni_3Mg_3)Si_4O_{10}(OH)_8$ |
| 3E | 158.4 | 145.6 | 124.5 | $(Ni_{1.5}Mg_{4.5})Si_4O_{10}(OH)_8$ |

(1) As polysilicic acid
(2) 80.77% active
(3) 96% active

Before calcination and reduction, all samples were admixed by wet mixing as before with montmorillonite as described in Example 1, in the proportion of 5% clay and 95% nickel serpentine.

The methanation catalytic activity and catalyst preparation were as in Example 2, with the following results:

Table VI

| | Methanation Activity: Minimum °C. for $\geq$ 90% CO Conversion | |
|---|---|---|
| Sample | * | ** |
| 3A | 210 | 300 |
| 3B | 210 | 250 |
| 3C | 240 | 250 |
| 3D | 240 | 240 |
| 3E | 260 | 500 |

*Catalyst reduced at 650° C. overnight.
**Catalyst reduced at 650° C. overnight and at 900° C. for three hours.

As may be seen from Table VI, all samples performed well, although sample 3E suffered somewhat from relatively low nickel content. The optimum content of nickel from a practical standpoint of course varies with the price of nickel at the time in question, so that one must balance cost against effectiveness. In times of high nickel prices, sample 3E would be considered satisfactory, while during times of low-nickel prices, one would naturally choose a nickel serpentine more along the lines of sample 3A, 3B, 3C, or 3D.

EXAMPLE 5

Some of the nickel serpentines described in Example 4 were tested for methanation activity, after forming into catalysts by calcining at 705° C. for three hours and hydrogen reduction at 650° C. overnight, for the conversion of carbon dioxide into methane. This reaction is more difficult to catalyze than that of carbon monoxide, as is generally recognized, although it does not have the same commercial importance as the methanation of the latter.

The nickel serpentines were mixed with 5% montmorillonite as already described, and the mesh size and catalyst charge were likewise the same as in the earlier examples. The feed gas was 15 mol % carbon dioxide and 85 mol % hydrogen. Results are shown in Table VII as follows:

Table VII

| Sample No. | °C. of run | Exit Gas Composition, Mol % CO | $H_2$ | $CH_4$ | $CO_2$ | Percent $CO_2$ Conversion |
|---|---|---|---|---|---|---|
| 3 C | 280 | 0 | 66.9 | 27.7 | 5.4 | 83.6 |
| | 300 | 0 | 62.1 | 35.3 | 2.6 | 93.1 |
| | 400 | 0 | 56.9 | 42.4 | 0.7 | 98.4 |
| | 500 | 0.4 | 61.9 | 34.6 | 3.1 | 91.9 |
| | 600 | 2.3 | 71.2 | 21.6 | 4.9 | 82.9 |
| 3 D | 300 | 0 | 82.0 | 14.8 | 3.2 | 82.2 |
| | 325 | 0 | 80.3 | 19.2 | 0.5 | 97.6 |
| | 400 | 0 | 81.1 | 18.9 | 0 | 100 |
| | 500 | 0.1 | 77.6 | 22.0 | 0.3 | 98.6 |
| | 600 | 0.5 | 79.7 | 16.8 | 2.0 | 90.1 |
| 3 E | 320 | 0 | 77.6 | 16.0 | 6.4 | 71.4 |
| | 340 | 0 | 76.3 | 20.1 | 3.6 | 85.0 |
| | 400 | 0 | 70.1 | 29.4 | 0.5 | 98.4 |
| | 500 | 0.2 | 72.7 | 25.9 | 1.2 | 95.5 |
| | 600 | 2.1 | 80.2 | 14.6 | 3.1 | 84.6 |

The excellent catalytic effectiveness for carbon dioxide methanation may be seen from Table VII. Substantial catalytic activity set in at around 350° C.

EXAMPLE 6

A natural nickel serpentine from Riddle, Oregon, was tested as a precursor for a methanation catalyst for carbon monoxide. The analysis of the material dried at 110° C. was as follows:

Table VIII

| Constituent | Weight Percent |
|---|---|
| NiO | 8.95 |
| $Fe_2O_3$ (total) | 3.59 |
| $Mn_2O_3$ | 0.04 |
| $Cr_2O_3$ | 0.01 |
| $TiO_2$ | 0.003 |
| CaO | 0.05 |
| $K_2O$ | 0.04 |
| $SiO_2$ | 44.51 |
| $Al_2O_3$ | 0.42 |
| MgO | 29.97 |
| $H_2O$ | 12.63 |
| Total: | 100.22 |

X-ray diffraction analysis showed a typical nickel serpentine, with a spacing of approximately 7 A.

The mineral, which had been ground to pass 200 mesh, was calcined in air at 705° C. for three hours, and then placed in the reactor, where it was reduced with hydrogen for fourteen hours at 650° C.

Using a gas feed of 20 mol percent carbon monoxide and 80 mol percent hydrogen, the following percent conversions were obtained:

Table IX

| Reactor Temperature,°C. | Percent CO Conversion |
|---|---|
| 300 | 58 |
| 350 | 90 |
| 400 | 100 |
| 450 | 99 |

These results are quite good, especially considering the relatively low nickel content of the sample, which was about 0.78 nickel atoms per unit cell, corresponding to y=0.67 in Formula [1].

The foregoing disclosure illustrates the manner of carrying out the invention, and shows many of the advantages thereof. It will be evident to those skilled in the art that in many methanation installations on a commercial scale, the oxides of carbon to be converted to methane will be present in a mixture of various components. Thus, carbon monoxide and carbon dioxide may both be present; and depending upon the source of the carbon oxides and of the hydrogen, more or less other gases such as nitrogen, water vapor and the like may be present. These will in general offer no bar to the successful carrying out of the invention.

In Equation [1], and in the discussion of the feed formula whereby the precursor nickel serpentines used in the invention may be formed, fluoride is shown as an optional component. In general this may be omitted without appreciably altering the behavior of the calcined catalyst. However it is sometimes an acid in crystallization from the starting feed mixture, and its optional inclusion has been set forth herein for that reason.

Angstrom units (one-tenth nanometer) have been abbreviated "A" in accordance with common usage, in this specification.

It will be understood that while we have explained the invention with the aid of specific examples, nevertheless considerable variation is possible in choice of raw materials, proportions, processing conditions, and the like, within the broad scope of the invention as set forth in the claims which follow. Thus, for example, our inventive catalyst may be used simultaneously with other catalytic materials, so as to suit particular conditions and circumstances. Further, the calcination and reduction may be carried out as separate or overlapping steps.

Having described the invention we claim:

1. In a process wherein a carbon oxide is catalytically hydrogenated so as to form methane by passing said carbon oxide together with hydrogen over a heated catalyst, the improvement which comprises utilizing as said catalyst an amorphous nickel silicate resulting from the calcination and reduction of a nickel serpentine having a chemical composition represented by the following:

$$(Ni_yR_gM_{6-y-g})\cdot(R_hSi_{4-h})O_{10}(OH,F)_8;$$

wherein:

M is Mg, Co$^{++}$, Fe$^{++}$, Cu$^{++}$, Mn$^{++}$, Zn$^{++}$, or mixtures thereof;

R is Al, Cr$^{+++}$, or mixtures thereof;

$$Zn \leqq 4, Cu \leqq 0.5, Mn \leqq 0.5,$$

$$g+h=2X$$
$$0 \leqq x < 0.1; 0.5 \leqq y \leqq 6;$$

and
wherein the first parenthesis shows the cations in the octahedral layer and the second parenthesis shows the cations in the tetrahedral layer; and wherein from zero to two fluoride ions may be present for a total of eight hydroxide plus fluoride; this precursor nickel serpentine prior to calcining being a 1:1 trioctahedral phyllosilicate in general having a substantially balanced framework, from the standpoint of total charge, with no exchangeable ions needed for neutrality, said calcination and reduction being carried out at a temperature of about 500° C. to about 900° C. and for a time sufficient to destroy the crystallinity of the precursor nickel serpentine and produce said amorphous nickel silicate, said reduction being performed in the presence of hydrogen wherein said nickel serpentine prior to said calcination is intimately admixed with up to about its own weight of clay mineral.

2. A process in accordance with claim 1 wherein M is Mg, and R is Al.

3. A process in accordance with claim 1 wherein said carbon oxide is a mixture of carbon monoxide and carbon dioxide.

4. A process in accordance with claim 2 wherein said carbon oxide is a mixture of carbon monoxide and carbon dioxide.

5. A process in accordance with claim 1 wherein said y has a value of between 1 and about 4.

6. A process in accordance with claim 2 wherein said y has a value of between 1 and about 4.

7. A process in accordance with claim 1 wherein said catalyst during said hydrogenation is heated to a temperature of at least about 200° C. but to a temperature high enough to effect substantial methanation of said carbon oxide.

8. A process in accordance with claim 1 in which said clay mineral is selected from the class consisting of montmorillonite, beidellite, kaolinite, halloysite, saponite, sepiolite, hectorite, attapulgite, illite, and mixtures thereof.

9. A process in accordance with claim 1 in which said admixing is brought about by wet mixing.

10. A process in accordance with claim 8 in which said admixing is brought about by wet mixing.

11. A process in accordance with claim 8 in which said clay mineral is selected from the group consisting of kaolinite, montmorillonite and mixtures thereof.

12. A process in accordance with claim 1 wherein M is Mg and x=0.

13. A process in accordance with claim 12 wherein $3.0 \leqq y \leqq 6.0$.

14. A process in accordance with claim 7 wherein said nickel serpentine is intimately admixed with up to about its own weight of a clay mineral.

15. A process in accordance with claim 7 wherein said clay mineral is selected from the group consisting of kaolinite, montmorillonite, beidellite, halloysite, saponite, sepiolite, hectorite, attapulgite, illite, and mixtures thereof.

16. A process in accordance with claim 14 wherein said clay mineral is selected from the group consisting of kaolinite, montmorillonite, and mixtures thereof.

17. A process in accordance with claim 15 wherein y=6.

* * * * *